(12) United States Patent
Gotou

(10) Patent No.: US 11,897,829 B2
(45) Date of Patent: Feb. 13, 2024

(54) METHOD FOR PRODUCING HYDRAULIC MEDIUM INCLUDING DIFLUOROETHYLENE

(71) Applicant: DAIKIN INDUSTRIES, LTD., Osaka (JP)

(72) Inventor: Tomoyuki Gotou, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 85 days.

(21) Appl. No.: 17/551,879

(22) Filed: Dec. 15, 2021

(65) Prior Publication Data

US 2022/0106242 A1   Apr. 7, 2022

Related U.S. Application Data

(63) Continuation of application No. PCT/JP2020/023679, filed on Jun. 17, 2020.

(30) Foreign Application Priority Data

Jun. 18, 2019   (JP) ................................. 2019-113131

(51) Int. Cl.
  *C07C 21/18*   (2006.01)
  *C07C 19/08*   (2006.01)

(52) U.S. Cl.
  CPC .............. *C07C 21/18* (2013.01); *C07C 19/08* (2013.01)

(58) Field of Classification Search
  CPC ......... C07C 21/18; C07C 19/08; C07C 17/42; C09K 2205/22; C09K 2205/126; C09K 5/04
  See application file for complete search history.

(56) References Cited

U.S. PATENT DOCUMENTS

| 9,969,917 | B2 | 5/2018 | Fukushima et al. |
| 2016/0333242 | A1 | 11/2016 | Fukushima et al. |
| 2016/0333243 | A1 | 11/2016 | Fukushima et al. |
| 2017/0138642 | A1* | 5/2017 | Ueno ........................ F24F 1/08 |

FOREIGN PATENT DOCUMENTS

| EP | 3 101 083 | 12/2016 |
| JP | 6432528 | 12/2018 |

OTHER PUBLICATIONS

International Search Report dated Sep. 8, 2020 in International (PCT) Application No. PCT/JP2020/023679.
Extended European Search Report dated Jun. 15, 2023 in European Patent Application No. 20827762.4.

* cited by examiner

*Primary Examiner* — Jafar F Parsa
(74) *Attorney, Agent, or Firm* — Wenderoth, Lind & Ponack, L.L.P.

(57) ABSTRACT

Provided is a method for producing a working medium containing difluoroethylene, the difluoroethylene not having self-decomposition properties.
A method for producing a working medium containing difluoroethylene.

15 Claims, 4 Drawing Sheets

Fig. 6
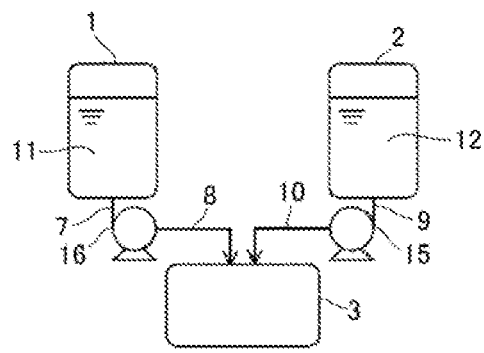
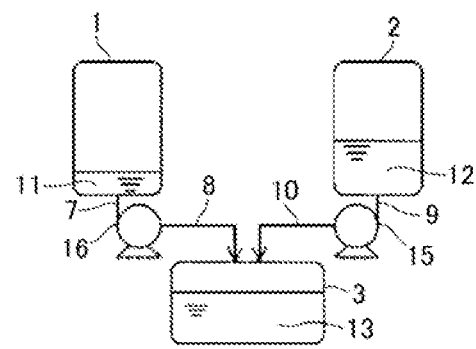

METHOD FOR PRODUCING HYDRAULIC MEDIUM INCLUDING DIFLUOROETHYLENE

TECHNICAL FIELD

The present disclosure relates to a method for producing a working medium containing difluoroethylene.

BACKGROUND ART

PTL 1 discloses a method for producing a working medium containing trifluoroethylene.

CITATION LIST

Patent Literature

PTL 1: JP6432528B

SUMMARY

Item 1. A method for producing a working medium containing difluoroethylene, comprising mixing a first component containing difluoroethylene at a ratio of more than 65 mol % and held in a first container, and a second component without self-decomposition properties held in a second container, by the following step (A), (B), or (C), the working medium containing difluoroethylene at a ratio of 65 mol % or less based on the entire amount.
Step (A)
The component held in the first container is supplied to the second container under the following condition (A1) or (A2).
Condition (A1)
The temperature (t1) of the component held in the first container at the time of the supply is t1<15° C., the relationship between the gauge pressure (P2) in the second container and the gauge pressure (p1) of the component held in the first container at the time of the supply is p1>P2 at least from the start of the supply to the end of the mixing, and the temperature (T2) in the second container is maintained in a state of T2<15° C.
Condition (A2)
The component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P2) in the second container and the gauge pressure (p1) of the component held in the first container is p1>P2 at least from the start of the supply to the end of the mixing, and the temperature (T2) in the second container is maintained in a state of T2≤180° C. and T2<(1.22−p1)/0.0032.
Step (B)
The component held in the second container is supplied to the first container under the following conditions (B1) and (B2).
Condition (B1) The temperature (T1) and gauge pressure (P1) in the first container are maintained in a state of T1<15° C. or in a state of 15° C.≤T1≤180° C. and P1 [MPaG]<1.22−0.0032T1 at least from the start of the supply to the end of the mixing.
Condition (B2)
The gauge pressure (p2) of the component held in the second container is p2>P1 at least at the time of the supply.

Step (C)
The component held in the first container is supplied to a separately prepared third container under the following condition (C1) or (C2), while maintaining the temperature (T3) and gauge pressure (P3) in the third container in a state of T3<15° C. or in a state of 15° C.≤T3≤180° C. and P3 [MPaG]<1.22−0.0032T3 at least from the start of the following supply to the end of the mixing, and the component held in the second container is supplied so that the gauge pressure (p2) thereof is p2>P3 at least at the time of supply thereof.
Condition (C1)
The temperature (t1) of the component held in the first container at the time of the supply is t1<15° C., the relationship between the gauge pressure (P3) in the third container and the gauge pressure (p1) of the component held in the first container at the time of the supply is p1>P3 at least from the start of the supply to the end of the mixing, and the temperature (T3) in the third container is maintained in a state of T3<15° C.
Condition (C2)
The component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P3) in the third container and the gauge pressure (p1) of the component held in the first container is p1>P3 at least from the start of the supply to the end of the mixing, and the temperature (T3) in the third container is maintained in a state of T3≤180° C. and T3<(1.22−p1)/0.0032.

Advantageous Effects of Invention

The present disclosure can produce a working medium containing difluoroethylene, the difluoroethylene not having self-decomposition properties.
The present disclosure can safely produce a working medium containing difluoroethylene, the difluoroethylene not undergoing a disproportionation reaction.

BRIEF DESCRIPTION OF DRAWINGS

FIG. 6 schematically shows an example of the operation to supply both the component held in the first container and the component held in the second container to the third container (step (C)) when the component held in the first container and the component held in the second container are both liquids at less than 15° C. in the present disclosure.

DESCRIPTION OF EMBODIMENTS

Figure 1:
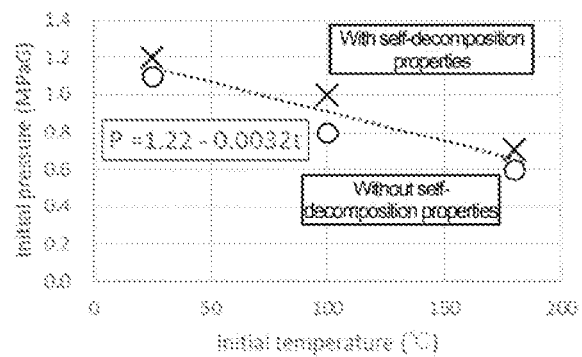
FIG. 1 is a graph showing the conditions of temperature (initial temperature) (t: ° C.) and pressure (gauge pressure) (initial pressure) (p: MPaG) in which difluoroethylene is self-decomposed in the present disclosure.

An object of the present disclosure is to provide a method for stably and efficiently producing, by an ordinary operation, a working medium that has less impact on global warming and that has excellent stability while containing difluoroethylene with excellent cycle performance.

Regarding the self-decomposition properties of difluoroethylene, the present inventor found that when a composition containing difluoroethylene had a difluoroethylene content of 65 mol % or less based on the entire amount of the composition, the composition did not have self-decomposition properties under temperature and pressure conditions for use as a working medium.

The present disclosure includes the following aspects.

The method for producing a working medium containing difluoroethylene of the present disclosure is a method for producing a working medium containing difluoroethylene, comprising mixing a component containing difluoroethylene at a ratio of more than 65 mol % and held in a first container, and a component without self-decomposition properties held in a second container, by the following step (A), (B), or (C), the working medium containing difluoroethylene at a ratio of 65 mol % or less based on the entire amount.

In step (A), the component held in the first container is supplied to the second container under the following condition (A1) or (A2).

In condition (A1), the temperature (t1) of the component held in the first container at the time of the supply is t1<15° C., the relationship between the gauge pressure (P2) in the second container and the gauge pressure (p1) of the component held in the first container at the time of the supply is p1>P2 at least from the start of the supply to the end of the mixing, and the temperature (T2) in the second container is maintained in a state of T2<15° C.

In condition (A2), the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P2) in the second container and the gauge pressure (p1) of the component held in the first container is p1>P2 at least from the start of the supply to the end of the mixing, and temperature (T2) in the second container is maintained in a state of T2≤180° C. and T2<(1.22−p1)/0.0032.

In step (B), the component held in the second container is supplied to the first container under the following conditions (B1) and (B2).

In condition (B1), the temperature (T1) and gauge pressure (P1) in the first container are maintained in a state of T1<15° C. or in a state of 15° C.≤T1≤180° C. and P1 [MPaG]<1.22−0.0032T1 at least from the start of the supply to the end of the mixing.

In condition (B2), the gauge pressure (p2) of the component held in the second container is p2>P1 at least at the time of the supply.

In step (C), the component held in the first container is supplied to a separately prepared third container under the following condition (C1) or (C2), while maintaining the temperature (T3) and gauge pressure (P3) in the third container in a state of T3<15° C. or in a state of 15° C.≤T3≤180° C. and P3 [MPaG]<1.22−0.0032T3 at least from the start of the following supply to the end of the mixing, and the component held in the second container is supplied so that the gauge pressure (p2) thereof is p2>P3 at least at the time of supply thereof.

In condition (C1), the temperature (t1) of the component held in the first container at the time of the supply is t1<15° C., the relationship between the gauge pressure (P3) in the third container and the gauge pressure (p1) of the component held in the first container at the time of the supply is p1>P3 at least from the start of the supply to the end of the mixing, and the temperature (T3) in the third container is maintained in a state of T3<15° C.

In condition (C2), the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P3) in the third container and the gauge pressure (p1) of the component held in the first container is p1>P3 at least from the start of the supply to the end of the mixing, and the temperature (T3) in the third container is maintained in a state of T3≤180° C. and T3<(1.22−p1)/0.0032.

(1) Working medium

The method for producing a working medium containing difluoroethylene of the present disclosure is a method for producing a working medium containing difluoroethylene, comprising mixing a component containing difluoroethylene at a ratio of more than 65 mol % and held in a first container, and a component without self-decomposition properties held in a second container, by step (A), (B), or (C) described later, the working medium containing difluoroethylene at a ratio of 65 mol % or less based on the entire amount.

In the method for producing a working medium containing difluoroethylene of the present disclosure, the difluoroethylene preferably contains at least one component held in a container selected from the group consisting of 1,1-difluoroethylene (HFO-1132a), cis-1,2-difluoroethylene (HFO-1132 (Z)), and trans-1,2-difluoroethylene (HFO-1132 (E)).

The working medium targeted by the production method of the present disclosure is a working medium containing difluoroethylene at a ratio of 65 mol % or less based on the entire amount of the working medium.

The present inventor confirmed that when a composition containing difluoroethylene had a difluoroethylene content of 65 mol % or less based on the entire amount of the composition, the composition did not have self-decomposition properties under temperature and pressure conditions for use as a working medium.

In the present disclosure, the self-decomposition properties of compositions containing difluoroethylene are evaluated by the following method. Those for which it is evaluated that a self-decomposition reaction occurs are regarded as having self-decomposition properties, and those for which it is evaluated that a self-decomposition reaction does not occur are regarded as not having self-decomposition properties.

(1-1) Evaluation of Self-Decomposition Properties of Difluoroethylene-Containing Composition The self-decomposition properties were evaluated using equipment conforming to method A recommended as the equipment for measuring the combustion range of a gas mixed with a halogen-containing gas in the individual notification under the High Pressure Gas Safety Act in Japan.

Difluoroethylene is at least one member selected from the group consisting of 1,1-difluoroethylene (HFO-1132a), cis-1,2-difluoroethylene (HFO-1132(Z)), and trans-1,2-difluoroethylene (HFO-1132(E)).

Specifically, in a spherical pressure-resistant container with an inner volume of 50 cm$^3$ controlled to a specific temperature from the outside, (a) a mixed medium of difluoroethylene and 2,3,3,3-tetrafluoropropene (HFO-1234yf), and (b) a mixed medium of difluoroethylene and difluoromethane (HFC-32), were sealed to a specific pressure (1.0 MPaG as gauge pressure). Then, a platinum wire placed inside the container was melted to apply about 30 J of energy.

Changes in temperature and pressure in the pressure-resistant container generated after energy application were measured to confirm the occurrence of a self-decomposition reaction.

When the pressure difference was 1 MPaG or more and the temperature difference was 10° C. or higher between before and after ignition, it was determined that a disproportionation reaction occurred.

Table 1 shows the self-decomposition reaction of (a) the mixed medium of difluoroethylene and 2,3,3,3-tetrafluoropropene (HFO-1234yf).

Table 2 shows the self-decomposition reaction of (b) the mixed medium of difluoroethylene and difluoromethane (HFC-32).

The pressures in Tables 1 and 2 are gauge pressures (MPaG).

hydrofluorocarbons, unsaturated hydrofluorocarbons, unsaturated hydrochlorofluorocarbons, and unsaturated chlorofluorocarbons.

These components do not have self-decomposition properties.

In the production method of the present disclosure, examples of such a compound (second component) include at least one component without self-decomposition properties selected from the group consisting of saturated hydrofluorocarbons, unsaturated hydrofluorocarbons (hereinafter also referred to as "HFCs"), unsaturated hydrochlorofluorocarbons (hereinafter also referred to as "HFOs"), and unsaturated chlorofluorocarbons (hereinafter also referred to as "CFOs"), described below.

In the production method of the present disclosure, examples of HFCs include HFC-32, difluoroethane, trifluoroethane, tetrafluoroethane, pentafluoroethane (HFC-125), pentafluoropropane, hexafluoropropane, heptafluoropropane, pentafluorobutane, heptafluorocyclopentane, and the like.

Of these, HFCs are preferably HFC-32, 1,1-difluoroethane (HFC-152a), 1,1,1-trifluoroethane (HFC-143a), 1,1,2,2-tetrafluoroethane (HFC-134), 1,1,1,2-tetrafluoroethane (HFC-134a), and HFC-125; more preferably HFC-32, HFC-134a, and HFC-125; and most preferably HFC-32, in terms of less influence on the ozone layer and excellent refrigeration cycle characteristics.

HFCs may be used singly or in combination of two or more.

In the production method of the present disclosure, examples of HFOs include HFO-1234yf, 1,2-difluoroethylene (HFO-1132), 2-fluoropropene (HFO-1261yf), 1,1,2-trifluoropropene (HFO-1243yc), trans-1,2,3,3,3-pentafluoropropene (HFO-1225ye(E)), cis-1,2,3,3,3-pentafluoropropene (HFO-1225ye(Z)), HFO-1234ze(E), cis-1,3,3,3-tetrafluoropropene (HFO-1234ze(Z)), 3,3,3-trifluoropropene (HFO-1243zf), and the like.

Of these, HFOs are preferably HFO-1234yf, HFO-1234ze (E), and HFO-1234ze(Z); and more preferably HFO-1234yf and HFO-1234ze(E).

HFOs may be used singly or in combination of two or more.

In the production method of the present disclosure, examples of CFOs include chlorofluoropropene, chlorofluoroethylene, and the like.

TABLE 1

| HFO-1132(E)/HFO-1234yf | | Pressure (MPaG) | | Temperature (° C.) | | Occurrence of self-decomposition reaction |
|---|---|---|---|---|---|---|
| (mass %/mass %) | (mol %/mol %) | Before ignition | After ignition | Before ignition | After ignition | |
| 55/45 | 69/31 | 1.0 | 1.0 | 250 | 250 | No occurrence |
| 60/40 | 73/27 | 1.0 | 5.0 | 250 | 300 | Occurrence |

TABLE 2

| HFO-1132(E)/HFC-32 | | Pressure (MPaG) | | Temperature (° C.) | | Occurrence of self-decomposition reaction |
|---|---|---|---|---|---|---|
| (mass %/mass %) | (mol %/mol %) | Before ignition | After ignition | Before ignition | After ignition | |
| 70/30 | 65/35 | 1.0 | 1.0 | 250 | 250 | No occurrence |
| 75/25 | 71/29 | 1.0 | 4.0 | 250 | 300 | Occurrence |

Tables 1 and 2 reveal that when the difluoroethylene content based on the entire amount of the composition is 65 mol % or less, the resulting compositions are highly stable. The compound (second component) to be combined with difluoroethylene (first component) to obtain a working medium is at least a compound that neither has self-decomposition properties nor destroys the ozone layer.

(1-2) Preferred Combination for Working Medium

In the method for producing a working medium containing difluoroethylene of the present disclosure, the component held in the second container is preferably at least one member selected from the group consisting of saturated Preferred CFOs are 1,1-dichloro-2,3,3,3-tetrafluoropropene (CFO-1214ya), 1,3-dichloro-1,2,3,3-tetrafluoropropene (CFO-1214yb), and 1,2-dichloro-1,2-difluoroethylene (CFO-1112), because they can easily suppress the flammability of working media without significantly reducing the cycle performance of the working media.

CFOs may be used singly or in combination of two or more.

In the method for producing a working medium containing difluoroethylene of the present disclosure, the component held in the second container preferably contains a component without self-decomposition properties at a ratio of 35 mol % or more.

The working medium targeted by the production method of the present disclosure preferably contains components (the component held in the second container and the component without self-decomposition properties), other than difluoroethylene (the first component held in the first container), at a ratio of 35 mol % or more. When combined with difluoroethylene within the above formulation range, the working medium is preferably one that has a low global warming potential (GWP) while having cycle performance that is practically sufficient to replace conventionally used R410A.

GWP is a value measured according to the 100-year value in the Fourth Assessment Report of the Intergovernmental Panel on Climate Change (IPCC) (2007).

In the method for producing a working medium containing difluoroethylene of the present disclosure, it is preferable that difluoroethylene (first component) is held in the first container, and that at least one component selected from the group consisting of 1,1-difluoroethylene (HFO-1132a), cis-1,2-difluoroethylene (HFO-1132(Z)), and trans-1,2-difluoroethylene (HFO-1132(E)) is contained as the difluoroethylene. Regarding the GWP of difluoroethylene, all of HFO-1132a, HFO-1132(Z), and HFO-1132(E) have a GWP of 1 or less.

When combined in the above formulation range, the compound to be combined with difluoroethylene is preferably a compound that can make the GWP of the resulting working medium to 2088 or less, which is the GWP value of R410A, more preferably 500 or less, even more preferably 300 or less, and particularly preferably 150 or less. In the present disclosure, the GWP of a mixture is the weighted average of the mass of each component in the mixture.

In the production method of the present disclosure, trifluoroethylene (HFO-1123) can also be used as HFO in combination with difluoroethylene.

When the working medium is made of a zeotropic mixture, there is a problem that it is difficult to restore the refrigerant formulation to the initial state. For example, the formulation changes during transfer from a pressure container to a refrigeration and air conditioning equipment, and if the refrigerant leaks from the refrigeration and air conditioning equipment, the refrigerant formulation in the refrigeration and air conditioning equipment is highly likely to change.

The working medium targeted by the production method of the present disclosure is preferably a pseudo-azeotropic mixed refrigerant, like R410A mentioned above, because the above problems can be avoided.

The "temperature gradient" described below is generally used as a measure of the above property of the mixture in the working medium. The temperature gradient is defined as a property of a heat exchanger where the starting and ending temperatures of, for example, evaporation in an evaporator or condensation in a condenser, are different. The temperature gradient is 0 in an azeotropic mixed refrigerant, and the temperature gradient is extremely close to 0 in a pseudo-azeotropic mixed refrigerant, like R410A.

Large temperature gradients are problematic because they increase the possibility of frost formation, for example, due to a decrease in the inlet temperature in the evaporator. Further, in order to improve the heat exchange efficiency in a heat cycle system, it is common practice to use a countercurrent between a working medium and a heat source fluid, such as water or air, flowing through the heat exchanger. Since the temperature difference in the heat source fluid is small in a stable operating state, it is difficult to obtain an energy-efficient heat cycle system in the case of a zeotropic mixed medium with a large temperature gradient.

Even when the working medium targeted by the production method of the present disclosure is a zeotropic mixed medium, the zeotropic mixed medium preferably has a moderately low temperature gradient.

In the method for producing a working medium containing difluoroethylene of the present disclosure, the component held in the second container is preferably 2,3,3,3-tetrafluoropropene (HFO-1234yf) and/or difluoromethane (HFC-32).

The working medium targeted by the production method of the present disclosure is preferably a working medium that well balances the above requirements of cycle performance, GWP, and temperature gradient, while solving the problem of self-decomposition caused by the single use of difluoroethylene. In the working medium targeted by the production method of the present disclosure, the compound to be combined with difluoroethylene is preferably HFO-1234yf and/or HFC-32.

The lower limit of the content of difluoroethylene in the working medium targeted by the present invention is preferably 35 mol %, and more preferably 40 mol %.

In the working medium targeted by the production method of the present disclosure, difluoroethylene is preferably at least one member selected from the group consisting of HFO-1132a, HFO-1132(Z), and HFO-1132(E). In the production method of the present disclosure, HFO-1123 can also be used as HFO in combination with difluoroethylene.

The formulation of the combination of difluoroethylene and HFO-1234yf and/or HFC-32 is specifically any of the following formulations, wherein the difluoroethylene content based on the entire amount of the working medium is 65 mol % or less.

(i) In the method for producing a working medium containing difluoroethylene of the present disclosure, the working medium obtained by mixing the component held in the first container and the component held in the second container is preferably a working medium containing difluoroethylene and HFO-1234yf, wherein the ratio of the total amount of difluoroethylene and HFO-1234yf based on the entire amount of the working medium is 65 mol % to 100 mol %, and the ratio of difluoroethylene based on the total amount of difluoroethylene and HFO-1234yf is 1 mol % to 65 mol %.

The working medium contains difluoroethylene and HFO-1234yf, the ratio of the total amount of difluoroethylene and HFO-1234yf based on the entire amount of the working medium is 65 mol % to 100 mol %, and the ratio of difluoroethylene based on the total amount of difluoroethylene and HFO-1234yf is 1 mol % to 65 mol %, preferably 10 mol % to 60 mol %, and more preferably 20 mol % to 60 mol %.

(ii) In the method for producing a working medium containing difluoroethylene of the present disclosure, the working medium obtained by mixing the component held in the first container and the component held in the second container is preferably a working medium containing difluoroethylene and HFC-32, wherein the ratio of the total amount of difluoroethylene and HFC-32 based on the entire amount of the working medium is 65 mol % to 100 mol %, and the ratio of difluoroethylene is 1 mol % to 65 mol % based on the total amount of difluoroethylene and HFC-32.

The working medium contains difluoroethylene and HFC-32, the ratio of the total amount of difluoroethylene and HFC-32 based on the entire amount of the working medium is 65 mol % to 100 mol %, and the ratio of difluoroethylene based on the total amount of difluoroethylene and HFC-32 is 1 mol % to 65 mol %, preferably 10 mol % to 60 mol %, and more preferably 20 mol % to 60 mol %.

(iii) In the method for producing a working medium containing difluoroethylene of the present disclosure, the working medium obtained by mixing the component held in the first container and the component held in the second container is preferably a working medium containing difluoroethylene, HFO-1234yf, and HFC-32, wherein the ratio of the total amount of difluoroethylene, HFO-1234yf, and HFC-32 based on the entire amount of the working medium is 65 mol % to 100 mol %, and based on the total amount of difluoroethylene, HFO-1234yf, and HFC-32, the ratio of difluoroethylene is 1 mol % to 65 mol %, the ratio of HFO-1234yf is 98 mol % or less, and the ratio of HFC-32 is 50 mol % or less.

The working medium contains difluoroethylene, HFO-1234yf, and HFC-32, wherein the ratio of the total amount of difluoroethylene, HFO-1234yf, and HFC-32 based on the entire amount of the working medium is 65 mol % to 100 mol %, and based on the total amount of difluoroethylene, HFO-1234yf, and HFC-32, the ratio of difluoroethylene is 1 mol % to 65 mol %, the ratio of HFO-1234yf is 98 mol % or less, and the ratio of HFC-32 is 50 mol % or less.

In the method for producing a working medium containing difluoroethylene of the present disclosure, the component held in the first container preferably comprises difluoroethylene.

In the method for producing a working medium containing difluoroethylene of the present disclosure, the component held in the second container preferably comprises a mixture of 2,3,3,3-tetrafluoropropene and difluoromethane.

In the method for producing a working medium containing difluoroethylene of the present disclosure, the component held in the second container preferably comprises trans-1,3,3,3-tetrafluoropropene.

In the method for producing a working medium containing difluoroethylene of the present disclosure, the component held in the second container preferably comprises a mixture of trans-1,3,3,3-tetrafluoropropene and difluoromethane.

(2) Production Method

The method for producing a working medium containing difluoroethylene of the present disclosure is a method for producing a working medium containing difluoroethylene, comprising mixing a component containing difluoroethylene at a ratio of more than 65 mol % and held in a first container, and a component without self-decomposition properties held in a second container, by the following step (A), (B), or (C), the working medium containing difluoroethylene at a ratio of 65 mol % or less based on the entire amount.

In step (A), the component held in the first container is supplied to the second container under the following condition (A1) or (A2).

In condition (A1), the temperature ($t_1$) of the component held in the first container at the time of the supply is $t_1 < 15°$ C., the relationship between the gauge pressure ($P_2$) in the second container and the gauge pressure ($p_1$) of the component held in the first container at the time of the supply is $p_1 > P_2$ at least from the start of the supply to the end of the mixing, and the temperature ($T_2$) in the second container is maintained in a state of $T_2 < 15°$ C.

In condition (A2), the component held in the first container at the time of the supply is in a gaseous state in which the temperature ($t_1$) thereof is $15°$ C. $\leq t_1 \leq 180°$ C. and the gauge pressure ($p_1$) thereof is $p_1$ [MPaG]$< 1.22 - 0.0032 t_1$, the relationship between the gauge pressure ($P_2$) in the second container and the gauge pressure ($p_1$) of the component held in the first container is $p_1 > P_2$ at least from the start of the supply to the end of the mixing, and the temperature ($T_2$) in the second container is maintained in a state of $T_2 \leq 180°$ C. and $T_2 < (1.22 - p_1)/0.0032$.

In step (B), the component held in the second container is supplied to the first container under the following conditions (B1) and (B2).

In condition (B1), the temperature ($T_1$) and gauge pressure ($P_1$) in the first container are maintained in a state of $T_1 < 15°$ C. or in a state of $15°$ C. $\leq T_1 \leq 180°$ C. and $P_1$ [MPaG]$< 1.22 - 0.0032 T_1$ at least from the start of the supply to the end of the mixing.

In condition (B2), the gauge pressure ($p_2$) of the component held in the second container is $p_2 > P_1$ at least at the time of the supply.

In step (C), the component held in the first container is supplied to a separately prepared third container under the following condition (C1) or (C2), while maintaining the temperature ($T_3$) and gauge pressure ($P_3$) in the third container in a state of $T_3 < 15°$ C. or in a state of $15°$ C. $\leq T_3 \leq 180°$ C. and $P_3$ [MPaG]$< 1.22 - 0.0032 T_3$ at least from the start of the following supply to the end of the mixing, and the second component is supplied so that the gauge pressure ($p_2$) thereof is $p_2 > P_3$ at least at the time of supply thereof.

In condition (C1), the temperature ($t_1$) of the component held in the first container at the time of the supply is $t_1 < 15°$ C., the relationship between the gauge pressure ($P_3$) in the third container and the gauge pressure ($p_1$) of the component held in the first container at the time of the supply is $p_1 > P_3$ at least from the start of the supply to the end of the mixing, and the temperature ($T_3$) in the third container is maintained in a state of $T_3 < 15°$ C.

In condition (C2), the component held in the first container at the time of the supply is in a gaseous state in which the temperature ($t_1$) thereof is $15°$ C. $\leq t_1 \leq 180°$ C. and the gauge pressure ($p_1$) thereof is $p_1$ [MPaG]$< 1.22 - 0.0032 t_1$, the relationship between the gauge pressure ($P_3$) in the third container and the gauge pressure ($p_1$) of the component held in the first container is $p_1 > P_3$ at least from the start of the supply to the end of the mixing, and the temperature ($T_3$) in the third container is maintained in a state of $T_3 \leq 180°$ C. and $T_3 < (1.22 - p_1)/0.0032$.

The production method of the present disclosure has any one of steps (A), (B), and (C) in order to mix the component held in the first container and the component held in the second container.

Each component and each step are described in detail below with reference to FIGS. 1 to 6.

(2-1) Component Held in First Container

The component held in the first container contains difluoroethylene at a ratio of more than 65 mol %. When the difluoroethylene content exceeds 65 mol %, the component held in the first container is likely to become self-decomposed. In the operation of mixing with the component held in the second container in the production method of the present disclosure, it is necessary to handle the component held in the first container under a condition in which it is not self-decomposed. When the difluoroethylene content is 100 mol %, the component held in the first container is most likely to become self-decomposed.

When conditions are set to ensure stability in steps (A), (B), and (C), if the conditions are set as if the component held in the first container consists of difluoroethylene, stability is ensured even when the difluoroethylene content of the component held in the first container is otherwise.

When the component held in the first container consists of 100 mol % of difluoroethylene, the self-decomposition properties thereof are controlled by the relationship between temperature (t) and pressure (p).

FIG. 1

FIG. 1 is a graph showing the conditions of temperature (t) and pressure (gauge pressure) (p) in which difluoroethylene (HFO-1132(E)) is self-decomposed. The dotted straight line denotes the boundary in the presence of self-decomposition properties. The formula represented by the straight line is p [MPaG]=1.22−0.0032t.

For reference, in the case of trifluoroethylene (HFO-1123), the formula represented by the straight line is p [MPaG]=1.13−0.0029t.

In FIG. 1, difluoroethylene has self-decomposition properties in a region above the straight line, and difluoroethylene does not have self-decomposition properties in a region below the straight line. That is, difluoroethylene does not have self-decomposition properties when p is less than 1.22−0.0032t.

Hereinafter, this straight line is also referred to as the "self-decomposition border line."

In FIG. 1, the self-decomposition properties are evaluated by the method described above under the temperature and pressure (gauge pressure) conditions, where the points indicated by ◯ are evaluated as not having self-decomposition properties, and the points indicated by X are evaluated as having self-decomposition properties. The above formula was obtained based on these measured values. "Before ignition" refers to the point of time when a mixed medium mixed at various ratios is sealed to a specific pressure and then a platinum wire placed inside is not melted, and "after ignition" refers to the point of time when a platinum wire is melted to apply about 30 J of energy.

In the production method of the present invention, the component held in the first container can be, for example, purified difluoroethylene obtained by distillation of crude difluoroethylene obtained by, for example, defluoridation of 1,1,2-trifluoroethane (HFC 143), wherein the difluoroethylene content is adjusted in the range of about 65 to 100 mole %.

The component held in the first container may contain compounds other than difluoroethylene at a ratio of less than 35 mol % based on the entire amount of the component held in the first container. Examples of compounds other than difluoroethylene that may be contained in the component held in the first container include by-products produced in the production of difluoroethylene, at least one member selected from the group consisting of saturated hydrofluorocarbons, unsaturated hydrofluorocarbons, unsaturated hydrochlorofluorocarbons, and unsaturated chlorofluorocarbons contained in the component held in the second container, and the like.

Regarding the conditions for ensuring stability during storage of the component held in the first container obtained in the above manner, if conditions that are stable when the difluoroethylene content is 100 mol %, at which self-decomposition is most likely to occur, are set, as in the above case, stability during storage is ensured even when the difluoroethylene content of the components held in the first container is otherwise.

Therefore, for the component held in the first container, an example of a case in which the difluoroethylene content is 100 mol % is described below.

Stability during storage is ensured when difluoroethylene is stored in a state in which the temperature (t) and pressure (p) thereof are p [MPaG]<1.22−0.0032t. If storage is possible in a state in which only a liquid of difluoroethylene is present in a specific container, stable storage without self-decomposition is possible.

FIG. 2

Figure 2:
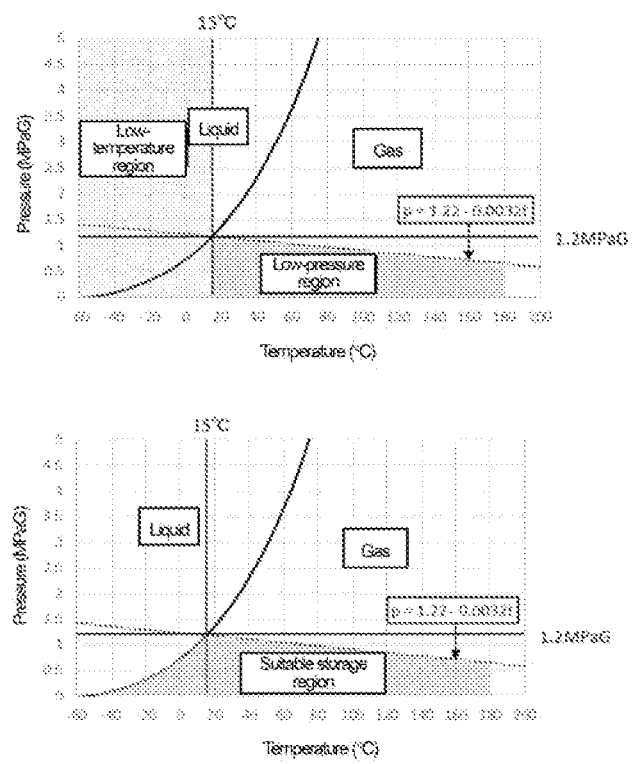
FIG. 2 is graphs showing a suitable storage region of difluoroethylene formed by superimposing a graph showing the relationship between the temperature of difluoroethylene and the vapor pressure on the graph of FIG. 1 in the present disclosure.

FIG. 2 shows graphs each showing the relationship between temperature and pressure at which difluoroethylene becomes a liquid (vapor pressure curve), superimposed on the graph of FIG. 1. In FIG. 2, the solid curve is a vapor pressure curve. Difluoroethylene is a gas in the region to the right of the vapor pressure curve, whereas difluoroethylene is a liquid in the left region. The state in which only a liquid of difluoroethylene is present, described above, refers to the liquid region to the left of the vapor pressure curve in FIG. 2.

In general, when a liquid of difluoroethylene is stored in a container, it is stored in a mixed gas-liquid state in which the difluoroethylene liquid and a gas coexist. The temperature and pressure in the mixed gas-liquid state are expressed as temperature and pressure on the vapor pressure curve; however, difluoroethylene is stable in the mixed gas-liquid state in a region at a temperature of 180° C. or less and below the self-decomposition border line. The specific region is below the intersection of the self-decomposition border line on the vapor pressure curve (temperature: 15° C., pressure: 1.2 MPaG).

Taking all this into account, the suitable storage region of difluoroethylene is the shaded area in FIG. 2b, that is, the area surrounded by a line of t=180° C., a line of p=1.22−0.0032t, and the vapor pressure curve, excluding the area on the line of p=1.22−0.0032t.

In the present disclosure, the "suitable storage region" of difluoroethylene is used as a term indicating the shaded area in FIG. 2b. Even when a liquid of difluoroethylene is stored in a container, stable storage at temperature and pressure in the liquid region to the left of the vapor pressure curve in FIG. 2 is possible if all the parts not filled with the liquid can be replaced by a gas other than difluoroethylene that does not affect the storage of difluoroethylene, e.g., nitrogen.

(2-2) Component Held in Second Container

The component held in the second container contains at least one member selected from the group consisting of saturated hydrofluorocarbons, unsaturated hydrofluorocarbons, unsaturated hydrochlorofluorocarbons, and unsaturated chlorofluorocarbons, at a ratio of 35 mol % or more. These components do not have self-decomposition properties.

Examples of the at least one member selected from the group consisting of saturated hydrofluorocarbons, unsaturated hydrofluorocarbons, unsaturated hydrochlorofluorocarbons, and unsaturated chlorofluorocarbons contained in the component held in the second container include the various compounds mentioned above. Preferred compounds and combinations thereof are also as described above. The component held in the second container may be a mixture containing difluoroethylene at a ratio of less than 65 mol % and not having self-decomposition properties.

When mixed with the component held in the first container at a specific ratio, the component held in the second container may have a formulation that can yield a working medium targeted by the production method of the present invention, that is, a working medium at least containing difluoroethylene at a ratio of 65 mol % or less. The formulation is preferably such that a working medium of any of the formulations (i) to (iii) described above can be obtained. From such a viewpoint, the component held in the second container preferably comprises HFO-1234yf and/or HFC-32.

Steps (A), (B), and (C)

In the production method of the present disclosure, the component held in the first container is prepared to be held in the first container, and the component held in the second container is prepared to be held in the second container. Then, the component held in the first container and the component held in the second container are mixed by any one of steps (A), (B), and (C).

In the production method of the present disclosure, the pressure is gauge pressure, unless otherwise specified.

(2-3) Step (A)

In the production method of the present disclosure, step (A) is a step of supplying the component held in the first container to a second container that holds the component held in the second container under condition (A1) or (A2).

In step (A), the component held in the first container is supplied to the second container under the following condition (A1) or (A2).

In condition (A1), the temperature (t1) of the component held in the first container at the time of the supply is t1<15° C., the relationship between the gauge pressure (P2) in the second container and the gauge pressure (p1) of the component held in the first container at the time of the supply is p1>P2 at least from the start of the supply to the end of the mixing, and the temperature (T2) in the second container is maintained in a state of T2<15° C.

In condition (A2), the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P2) in the second container and the gauge pressure (p1) of the component held in the first container is p1>P2 at least from the start of the supply to the end of the mixing, and the temperature (T2) in the second container is maintained in a state of T2≤180° C. and T2<(1.22−p1)/0.0032.

In the method for producing a working medium containing difluoroethylene of the present disclosure, it is preferable that in step (A), the temperature in the first container and the temperature in the second container are both maintained at less than 15° C., and that the component held in the first container is supplied in a liquid state at t1<15° C. to the second container.

The conditions defined in the following (A1) and (A2) relate to the temperature (t1) and pressure (p1) of the component held in the first container when the component held in the first container is supplied to the second container, and the temperature (T2) and pressure (P2) in the second container at least from the start of supply of the component held in the first container to the second container to the end of mixing of the component held in the first container and the component held in the second container performed in the second container after the supply.

In the present disclosure, the temperature and pressure "at the time of supply" refer to the temperature and pressure at the time when the component held in a certain container enters another container. Unless otherwise specified, when the supply is performed continuously, a constant state is maintained from the start to the end of the supply.

All of these conditions in step (A) are set based on the conditions that are stable when the difluoroethylene content of the component held in the first container is 100 mol %. This suggests that the above conditions in step (A) can ensure stability even when a component of any formulation within the specified range held in the first container is mixed with a component of any formulation held in the second container to produce a working medium of any formulation.

The condition setting made on the basis of the conditions that are stable when the difluoroethylene content of the component held in the first container is 100 mole % is also applied to steps (B) and (C), described later. Therefore, it can be said that stability can also be ensured in steps (B) and (C), as in step (A).

In condition (A1), the temperature (t1) of the component held in the first container at the time of the supply is t1<15° C., the relationship between the gauge pressure (P2) in the second container and the gauge pressure (p1) of the component held in the first container at the time of the supply is p1>P2 at least from the start of the supply to the end of the mixing, and the temperature (T2) in the second container is maintained in a state of T2<15° C.

In condition (A2), the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P2) in the second container and the gauge pressure (p1) of the component held in the first container is p1>P2 at least from the start of the supply to the end of the mixing, and the temperature (T2) in the second container is maintained in a state of T2≤180° C. and T2<(1.22−p1)/0.0032.

The condition common in conditions (A1) and (A2) of step (A) relates to a pressure at which the relationship between the pressure (p1) of the component held in the first container and the pressure (P2) in the second container is p1>P2 when the component held in the first container is supplied to the second container. This pressure condition is essential when the component held in the first container is supplied to the second container. (A1) and (A2) each show the relationship between the temperature (t1) and pressure (p1) of the component held in the first container and the temperature (T2) in the second container at the time of supply under the essential pressure condition of p1>P2 when the component held in the first container is supplied to the second container.

In step (A), the temperature (T2) and pressure (P2) in the second container may be in the state of (A1) or (A2) above at least from the start of supply of the component held in the first container to the end of mixing of the component held in the first container and the component held in the second container performed in the second container after the supply.

At the end of the mixing, a working medium of a stable formulation in the embodiment of the present invention is obtained as a reservoir in the second container. Thus, neither the component held in the second container accommodated in the second container, nor the working medium according to the embodiment of the present disclosure, has self-decomposition properties before the start of the supply and after the end of mixing. There is no particular point to pay attention to handling from the viewpoint of self-decomposition. The end of the mixing is generally the point of time when the supply of the component held in the first container is stopped, as described later.

The temperature (T1) and pressure (P1) in the first container that holds the component held in the first container are always maintained in the range of the conditions that are stable even when the difluoroethylene content of the component held in the first container is 100 mol % described above, preferably in the region at 180° C. or less and below the self-decomposition border line, and more preferably within the suitable storage region.

In general, when the component held in the first container is supplied to the second container that holds the component held in the second container, a supply pipe is provided to connect the first container and the second container, and the component held in the first container is supplied through the supply pipe to the second container. The supply pipe that connects the first container and the second container generally has means for turning on and off the supply of the component held in the first container and controlling the amount of supply per hour, and also has, if necessary, a pressure adjusting means and a temperature adjusting means. In step (A), in order to achieve p1>P2, which is an essential condition for this step, a pressure adjusting means, typically a pump, provided in the supply pipe is generally used.

The temperature (t1) and pressure (p1) of the component held in the first container at the time of supply do not necessarily match the temperature and pressure conditions of the component held in the first container maintained at the temperature (T1) and pressure (P1) in the first container. FIG. 2 shows a filled-in area that is the range of possible temperatures (t1) and pressures (p1) of the component held in the first container at the time of supply in order to stably supply the component held in the first container into the second container.

When the temperature (t1) and pressure (p1) of the component held in the first container at the time of supply are in the filled-in region at t1<15° C. of condition (A1) (hereinafter referred to as the "low-temperature region"), or in the gas region at 15° C.≤t1≤180° C. and p1 [MPaG] <1.22−0.0032t1, as indicated by the grid pattern, of conditions (A2) (hereinafter referred to as the "low-pressure region") in FIG. 2, the temperature (T2) in the second container is set to a specific condition, specifically each of conditions (A1) and (A2), under the pressure condition of p1>P2, whereby the component held in the first container can be stably supplied. In this case, it is preferable to adjust the amount of supply per hour of the component held in the first container to the second container.

(A1) is condition setting for supplying the component held in the first container in the low-temperature region to the second container at a lower pressure in the same temperature region. If this condition is satisfied, the stability of the second container can be ensured.

(A2) is condition setting for supplying the component held in the first container in the low-pressure region to the second container at a lower pressure and a temperature (T2) of 180° C. or less and in a state in which the pressure (p1) is still below the self-decomposition border line even if the temperature (t1) of the component held in the first container increases to the temperature (T2) in the second container. If this condition is satisfied, the stability of the second container can be ensured.

When the component held in the first container is mixed with the component held in the second container, it is preferable to mix both components in a liquid state, in terms of efficiency. In order to apply this condition, for example, the component held in the first container is held as a liquid at less than 15° C. in the first container. In general, it is preferable to store the component held in the first container in a state in which gas and liquid coexist. The temperature and pressure in the first container are preferably adjusted at a temperature of less than 15° C. and on the vapor pressure curve of difluoroethylene.

When the component held in the first container is supplied as a liquid to the second container, the temperature (t1) and pressure (p1) of the component held in the first container at the time of supply are adjusted to satisfy p1>P2 and to be in the low-temperature region and in the liquid region. In this case, the temperature condition in the second container is in a state of T2<15° C. according to (1) above. The component held in the second container is preferably in a liquid state. Conditions under which the second container is placed, that is, conditions in which the component held in the second container becomes a liquid in the range of p1>P2 and T2<15° C., are selected.

FIG. 3

Figure 3:
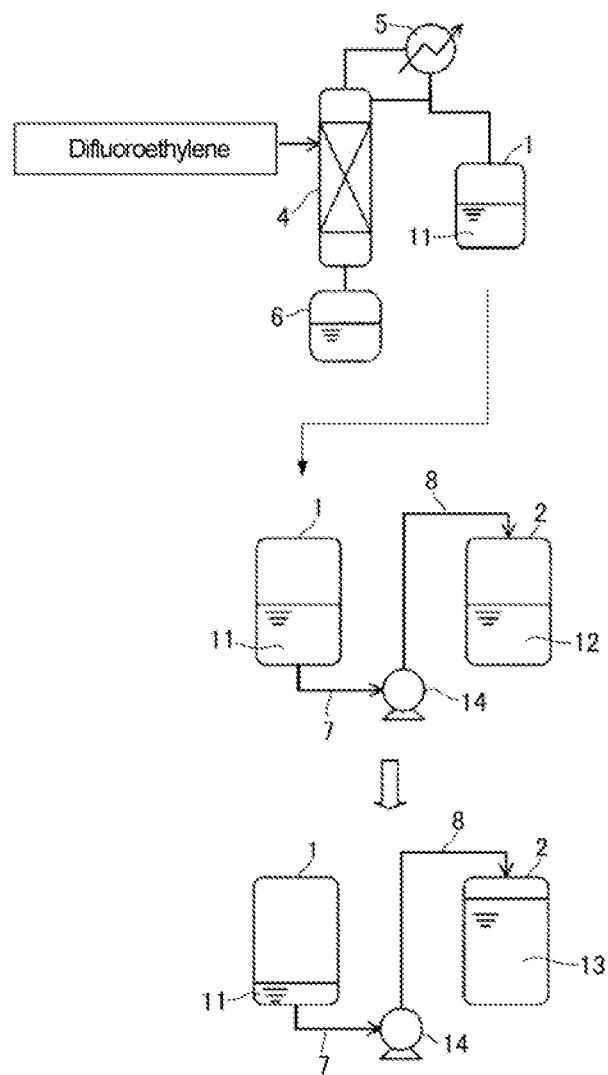
FIG. 3 schematically shows an example of the operation to supply the component held in the first container to the second container (step (A)) when the component held in the first container and the component held in the second container are both liquids at less than 15° C. in the present disclosure.

FIG. 3 schematically shows an example of step (A) when the component held in the first container and the component held in the second container are both liquids at less than 15° C.

In FIG. 3 (4a), as a component 11 held in a first container, crude difluoroethylene obtained by, for example, defluoridation of 1,1,2-trifluoroethane (HFC 143) is supplied to a distiller 4, by-products are removed as a bottom product in a bottom product storage tank 6, and the distillate obtained from the top of the column is passed through a cooling condensing means 5 to obtain a distillation liquid, thereby preparing difluoroethylene (liquid). Difluoroethylene (liquid) 11 is obtained stored in the first container 1. The component held in the first container may be a component (held in the first container) placed in a commercially available container.

In FIG. 3, difluoroethylene (liquid) 11 obtained stored in the first container 1 is supplied to a separately prepared second container 2 in which a component (liquid) 12 held in the second container is stored. FIG. 3 (4b) shows a state of the component 11 held in the first container before being supplied to the second container 2, and FIG. 3 (4c) shows a state in which the first component 11 is supplied to the second container 2 to obtain a working medium 13. As with the component held in the first container, the component held in the second container is produced by a known method, and may be a bottom product or distillate obtained by purification by distillation stored in the second container, or a component (held in the second container) placed in a commercially available container.

For example, the temperature (T1) in the first container 1 is less than 15° C., and the pressure (P1) is adjusted to a pressure at which the component held in the first container becomes a liquid, specifically, a pressure on the vapor pressure curve at −50° C. or more and less than 15° C. The temperature and pressure of the component held in the first container within the first container 1 are the same as the temperature (T1) and pressure (P1) in the first container.

In FIG. 3, the first container 1 has a discharge port, the second container 2 has a supply port, and these ports are connected through a pump 14 by a supply pipe 7 and a supply pipe 8, through which gas or liquid can flow. The component 11 held in in the first container within the first container 1 moves from the discharge port of the first container 1 to the supply port of the second container 2 within the supply pipe 7 and supply pipe 8 through the pump 14, and is supplied into the second container 2. The supply pipe 7 connects the discharge port of the first container 1 and the pump 14, and the supply pipe 8 connects the pump 14 and the supply port of the second container 2.

The second container 2 is set and maintained so that the temperature (T2) is less than 15° C. and the pressure (P2) is a pressure at which the component held in the second container 2 is in a liquid state.

When the pressure (P2) in the second container 2 is lower than the pressure (P1) in the first container 1, the component held in the first container is generally moved by its self-pressure. In this case, the pressure (p1) and temperature (t1) of the component held in the first container at the time of supply to the second container are the same as the temperature (T1) and pressure (P1) in the first container. In this case, the pressure relationship is P1=p1>P2.

When the pressure (P2) is higher than the pressure (P1), the pressure (p1) of the component held in the first container at the time of supply is increased to higher than the pressure (P2) in the second container 2 by the pump 14. In this case, the temperature (t1) of the component held in the first container after pressurization is not necessarily the same as the temperature (T1) before pressurization; however, pressurization is performed within the range in which the temperature is maintained at less than 15° C. That is, the component held in the first container is supplied as a liquid in the low-temperature region into the second container.

In FIG. 3, in this case, the temperature and pressure of the component held in the first container within the supply pipe 7 that connects the first container 1 and the pump 14 are the same as the temperature (T1) and pressure (P1) in the first container 1. On the other hand, the temperature and pressure of the component held in the first container within the supply pipe 8 that connects the pump 14 and the second container 2 are the same as the temperature (t1) and pressure (p1) of the component held in the first container at the time of supply. The pressure relationship is P1<P2<p1.

In this example, the conditions for performing step (A) correspond to (A1) above. Therefore, the temperature (T2) in the second container 2 is maintained at less than 15° C. at least from the start of supply of the component held in the first container to the end of mixing of the component held in the first container and the component held in the second container.

In FIG. 3, due to the supply of the component 11 held in the first container into the second container 2 in this manner, the component 12 held in the second container and the component 11 held in the first container are mixed in the second container 2. The supply of the component 11 held in the first container is stopped when the reservoir in the second container 2 has the formulation of the target working medium 13. The supply of the component 11 held in the first container is preferably stopped when the formulation of the target working medium 13 is measured by a means capable of continuously measuring the formulation of the reservoir in the second container 2. The amounts of the component held in the first container and the component held in the second container to be mixed may be adjusted in advance according to the formulation of the target working medium 13.

Figure 4:
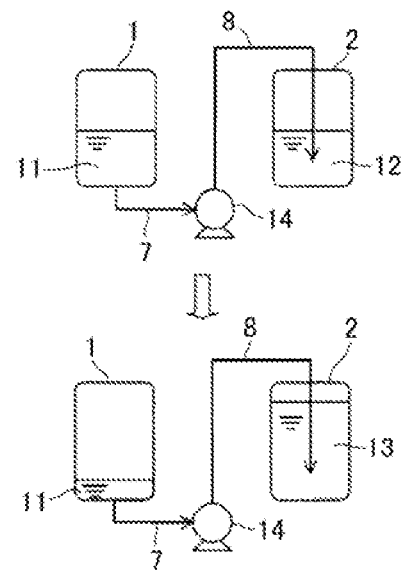
FIG. 4 schematically shows another example of the operation to supply the component held in the first container to the second container (step (A)) when the component held in the first container and the component held in the second container are both liquids at less than 15° C. in the present disclosure.

When the component held in the first container and the component held in the second container are both liquids at less than 15° C., step (A) can be performed, for example, as shown in FIG. 4. FIG. 4 schematically shows the operation to supply the component held in the first container in a liquid state into a liquid of the component held in the second container when performing step (A) using the component held in the first container and the component held in the second container both as liquids at less than 15° C.

In the method shown in FIG. 3, the supply pipe 8 is provided to connect the pump 14 and the supply port of the second container 2.

FIG. 4

In the method shown in FIG. 4, the supply pipe 8 is provided so that one end thereof is connected to the pump 14 and the other end reaches the component (liquid) 12 held in the second container from the pump 14 through the supply port of the second container 2. There is no other difference. In the method shown in FIG. 4, the conditions for performing step (A) when the component held in the first container and the component held in the second container are both liquids at less than 15° C. described above remain the same.

For example, as shown in FIG. 4, the advantage of supplying the component held in the first container in a liquid state into a liquid of the component held in the second container is that mixing of the component held in the second container and the component held in the first container is promoted.

(2-4) Step (B)

In the production method of the present disclosure, step (B) is a step of supplying the component held in the second container to the first container that holds the component held in the first container under the following conditions (B1) and (B2).

In step (B), the component held in the second container is supplied to the first container under the following conditions (B1) and (B2).

In condition (B1), the temperature (T1) and gauge pressure (P1) in the first container are maintained in a state of T1<15° C. or in a state of 15° C.≤T1≤180° C. and P1 [MPaG]<1.22−0.0032T1 at least from the start of the supply to the end of the mixing.

In condition (B2), the gauge pressure (p2) of the component held in the second container is p2>P1 at least at the time of the supply.

In the method for producing a working medium containing difluoroethylene of the present disclosure, it is preferable that in step (B), the temperature in the first container and the temperature in the second container are both maintained at less than 15° C., and that the component held in the second container is supplied in a liquid state at t2<15° C. to the first container.

Condition (B2) in step (B) relates to a pressure at which the relationship between the pressure (p2) of the component held in the second container and the pressure (P1) in the first container is p2>P1 when the component held in the second container is supplied to the first container. This pressure condition is essential when the component held in the second container is supplied to the first container.

In condition (B1), the temperature (T1) and pressure (P1) in the first container are maintained in the low-temperature region or the low-pressure region shown in FIG. 2 at least from the start of supply of the component held in the second container to the first container to the end of mixing of the component held in the first container and the component held in the second container performed in the first container after the supply. The end of the mixing is generally the point of time when the supply of the component held in the second container is stopped.

Before the start of supply of the component held in the second container, the temperature (T1) and pressure (P1) in the first container that holds the component held in the first container are maintained in the range of the conditions that are stable even when the difluoroethylene content of the component held in the first container is 100 mol % shown above, preferably in the region at 180° C. or less and below the self-decomposition border line, and more preferably within the suitable storage region. Further, at the end of the mixing, a working medium of a stable formulation in the embodiment of the present invention is obtained as a reservoir in the first container. This working medium does not have self-decomposition properties. Accordingly, from the viewpoint of self-decomposition, there is no particular point to pay attention to the handling of the first container after the end of the mixing.

In step (B), the temperature (T2) and pressure (P2) in the second container 2 are not limited. The temperature and pressure of the component held in the second container within the second container 2 are the same as the temperature (T2) and pressure (P2); however, the temperature (t2) and pressure (p2) of the component held in the second container at the time of supply to the first container 1 can be adjusted, for example, by the following means.

In general, when the component held in the second container is supplied to the first container that holds the component held in the first container, a supply pipe is provided to connect the second container and the first container, and the component held in the second container is supplied through the supply pipe to the first container. The supply pipe that connects the first container and the second container generally has means for turning on and off the supply of the component held in the second container and controlling the amount of supply per hour, and also has, if necessary, a pressure adjusting means and a temperature adjusting means. In step (B), in order to achieve p2>P1, which is an essential condition for this step, a pressure adjusting means, typically a pump, provided in the supply pipe is generally used.

In step (B), in order to maintain the temperature (T1) and pressure (P1) in the first container within the low-temperature region or low-pressure region shown in FIG. 2 from the start of supply of the component held in the second container to the end of the mixing, the temperature (t2) and pressure (p2) of the component held in the second container at the time of supply to the first container, and further the amount of supply per hour, are adjusted so that the temperature (T1) and pressure (P1) are within the above range.

For example, when the temperature (T1) and pressure (P1) in the first container are in the low-temperature region, the temperature (t2) and pressure (p2) of the component held in the second container at the time of supply are set within the low-temperature region. Further, when the temperature (T1) and pressure (P1) in the first container are in the low-pressure region, for example, the temperature (t2) and pressure (p2) of the component held in the second container at the time of supply are set within the low-pressure region.

In this case, in more stable conditions, for example, the pressure (p2) is within the low-pressure region and t2< (1.22−P1)/0.0032.

In step (B), if efficiency is important, it is also preferable to mix the component held in the first container and the component held in the second container both in a liquid state, as in step (A) above.

In order to apply this condition, for example, the component held in the first container is maintained as a liquid at less than 15° C. in the first container before the component held in the second container is supplied. In general, it is preferable to store the component held in the first container in a state in which gas and liquid coexist. The temperature and pressure in the first container are preferably adjusted at a temperature of less than 15° C. and on the vapor pressure curve of difluoroethylene before the component held in the second container is supplied.

The component held in the second container is supplied in a liquid state at less than 15° C. at p2>P1 to the first container in such a state so as to comply with conditions (B1) and (B2), and mixed with the component held in the first container as a liquid at a temperature of less than 15° C. and on the vapor pressure curve of difluoroethylene. In step (B), the component held in the first container and the component held in the second container can be preferably mixed both in a liquid state in the above manner.

FIG. 5

Figure 5:
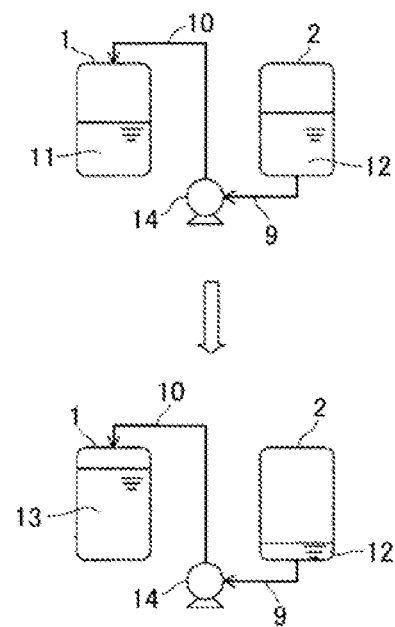
FIG. 5 schematically shows an example of the operation to supply the component held in the second container to the first container (step (B)) when the component held in the first container and the component held in the second container are both liquids at less than 15° C. in the present disclosure.

FIG. 5 schematically shows an example of step (B) when the component held in the first container and the component held in the second container are both liquids at less than 15° C. The first container 1 that holds the component 11 held in the first container and the second container 2 that holds the component 12 held in the second container can be prepared in the same manner as in step (A) above.

FIG. 5 shows the operation to supply the component (liquid) 12 held in the second container 2 to the first container 1 that holds the component (liquid) 11 held in the first container. FIG. 5 (6a) shows a state of the component 12 held in the second container before being supplied to the first container 1, and FIG. 5 (6b) shows a state in which the component 12 held in the second container is supplied to the first container 1 to obtain a working medium 13.

In FIG. 5 (6a), for example, the temperature (T1) in the first container 1 is less than 15° C., as described above, and the pressure (P1) is adjusted to a pressure at which the component held in the first container becomes a liquid, specifically a pressure on the vapor pressure curve at −50° C. or more and less than 15° C. The temperature and pressure of the component held in the first container within the first container 1 are the same as the temperature (T1) and pressure (P1) in the first container.

In FIG. 5, the second container 2 has a discharge port, the first container 1 has a supply port, and these ports are connected through a pump 14 by a supply pipe 9 and a supply pipe 10, through which gas or liquid can flow. The component 12 held in the second container within the second container 2 moves from the discharge port of the second container 2 through the pump 14 in the supply pipe 9 and supply pipe 10 to the supply port of the first container 1, and is supplied into the first container 1. The supply pipe 9 connects the discharge port of the second container 2 and the pump 14, and the supply pipe 10 connects the pump 14 and the supply port of the first container 1.

In FIG. 5, the second container 2 is set and maintained so that the temperature (T2) is less than 15° C. and the pressure (P2) is a pressure at which the component held in the second container 2 is in a liquid state. When the pressure (P1) in the first container 1 is lower than the pressure (P2) in the second container 2, the component held in the second container is generally moved by its self-pressure. In this case, the pressure (p2) and temperature (t2) of the component held in the second container at the time of supply to the first container are the same as the temperature (T2) and pressure (P2) in the second container. In this case, the pressure relationship is P2=p2>P1.

In FIG. 5, when the pressure (P1) is higher than the pressure (P2), the pressure (p2) of the component held in the second container at the time of supply is increased to higher than the pressure (P1) in the first container 1 by the pump 14. In this case, the temperature (t2) of the component held in the second container after pressurization is not necessarily the same as the temperature (T2) before pressurization; however, pressurization is performed within the range in which the temperature is maintained at less than 15° C. That is, the component held in the second container is supplied as a liquid in the low-temperature region into the first container. In this case, the temperature and pressure of the component held in the second container in the supply pipe 9 that connects the second container 2 and the pump 14 are the same as the temperature (T2) and pressure (P2) in the second container 2. On the other hand, the temperature and pressure of the component held in the second container in the supply pipe 10 that connects the pump 14 and the first container 1 are the same as the temperature (t2) and pressure (p2) of the component held in the second container at the time of supply. The pressure relationship is P2<P1<p2.

In this example, the conditions for performing step (B) depend on (B1) and (B2) mentioned above. Therefore, the temperature (T1) in the first container 1 is maintained at less than 15° C. at least from the start of supply of the component held in the second container to the end of mixing of the component held in the second container and the component held in the first container.

In FIG. 5, the component 12 held in the second container is thus supplied into the first container 1, whereby the component 12 held in the second container and the component 11 held in the first container are mixed in the first container 1. The supply of the component 12 held in the second container is stopped when the reservoir in the first container 1 has the formulation of the target working medium 13. The supply of the component 12 held in the second container is preferably stopped when the formulation of the target working medium 13 is measured by a means capable of continuously measuring the formulation of the reservoir in the first container 1. The amounts of the component held in the first container and the component held in the second container to be mixed may be adjusted in advance according to the formulation of the target working medium 13.

When step (B) is performed using the component held in the first container and the component held in the second container both as liquids at less than 15° C., the second component may be supplied in a liquid state into a liquid of the component held in the first container. The advantage of thus supplying the component held in the second container in a liquid state into the liquid of the component held in the first container is that mixing of the component held in the second container and the component held in the first container is promoted.

(2-5) Step (C)

In step (C) of the production method of the present disclosure, the temperature (T3) and gauge pressure (P3) in a separately prepared third container are maintained in a state of T3<15° C. (low-temperature region) or in a state of 15° C.≤T3≤180° C. and P3 [MPaG]<1.22−0.0032T3 (low-pressure region) at least from the start of the following supply to the third container to the end of the mixing. In this step, the component held in the first container is supplied under the following condition (C1) or (C2), and the component held in the second container is supplied so that the gauge pressure (p2) thereof is p2>P3 at least at the time of supply.

The conditions defined in the following (C1) and (C2) relate to the temperature (t1) and pressure (p1) of the component held in the first container when the component held in the first container is supplied to the third container, and the temperature (T3) and pressure (P3) in the third container at least from the start of supply of the component held in the first container to the third container to the end of mixing of the component held in the first container and the component held in the second container performed in the third container after the supply.

These conditions are set in the case of changing the second container under the conditions defined in (A1) and (A2) of step (A) to the third container, and are the same except that the temperature (T2) and pressure (P2) in the second container are replaced by the temperature (T3) and pressure (P3) in the third container.

In step (C), the component held in the first container is supplied to a separately prepared third container under the following condition (C1) or (C2), while maintaining the temperature (T3) and gauge pressure (P3) in the third container in a state of T3<15° C. or in a state of 15° C.≤T3≤180° C. and P3 [MPaG]<1.22−0.0032T3 at least from the start of the following supply to the end of the mixing, and the component held in the second container is supplied so that the gauge pressure (p2) thereof is p2>P3 at least at the time of supply thereof.

In condition (C1), the temperature (t1) of the component held in the first container at the time of the supply is t1<15° C., the relationship between the gauge pressure (P3) in the third container and the gauge pressure (p1) of the component held in the first container at the time of the supply is p1>P3 at least from the start of the supply to the end of the mixing, and the temperature (T3) in the third container is maintained in a state of T3<15° C.

In condition (C2), the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P3) in the third container and the gauge pressure (p1) of the component held in the first container is p1>P3 at least from the start of the supply to the end of the mixing, and the temperature (T3) in the third container is maintained in a state of T2≤180° C. and T3<(1.22−p1)/0.0032.

In the method for producing a working medium containing difluoroethylene of the present disclosure, it is preferable that in step (C), the temperature in the first container, the temperature in the second container, and the temperature in the third container are all maintained at less than 15° C., and that the component held in the first container is supplied in a liquid state at t1<15° C., and the component held in the second container is supplied in a liquid state at t2<15° C., to the third container.

The condition common in conditions (C1) and (C2) of step (C) relates to a pressure at which the relationship between the pressure (p1) of the component held in the first container and the pressure (P3) in the third container is p1>P3 when the component held in the first container is supplied to the third container.

This pressure condition is essential when the component held in the first container is supplied to the third container. (C1) and (C2) each show the relationship between the temperature (t1) and pressure (p1) of the component held in the first container and the temperature (T3) in the third container at the time of supply under the essential pressure condition, i.e., p1>P3, when the component held in the first container is supplied to the third container.

In step (C), the temperature (T3) and pressure (P3) in the third container may be in the state of (C1) or (C2) above at least from the start of supply of the component held in the first container and the component held in the second container to the end of mixing of the component held in the first container and the component held in the second container performed in the third container after the supply.

At the end of the mixing, a working medium of a stable formulation in the embodiment of the present disclosure is obtained as a reservoir in the third container. There is no reservoir in the third container before the start of the supply. The working medium according to the embodiment of the present disclosure, which is accommodated in the third container after the end of mixing, does not have self-decomposition properties.

From the viewpoint of self-decomposition, there is no particular point to pay attention to the handling of the third container before the start of the supply and after the end of mixing. The end of the mixing is generally the point of time when the supply of the component held in the first container is stopped, as described later.

The temperature (T1) and pressure (P1) in the first container that holds the component held in the first container are always maintained in the range of the conditions that are stable even when the difluoroethylene content of the component held in the first container is 100 mol % shown above, preferably in the region at 180° C. or less and below the self-decomposition border line, and more preferably within the suitable storage region.

In general, when the component held in the first container is supplied to the third container, a supply pipe is provided to connect the first container and the third container, and the component held in the first container is supplied through the supply pipe to the third container. The supply pipe that connects the first container and the third container generally has means for turning on and off the supply of the component held in the first container and controlling the amount of supply per hour, and also has, if necessary, a pressure adjusting means and a temperature adjusting means. In step (C), in order to achieve p1>P3, which is an essential condition for this step, a pressure adjusting means, typically a pump, provided in the supply pipe is generally used.

Thus, the temperature (t1) and pressure (p1) of the component held in the first container at the time of supply do not necessarily match the temperature and pressure conditions of the component held in the first container that is maintained at the temperature (T1) and pressure (P1) in the first container. When the temperature (t1) and pressure (p1) of the component held in the first container at the time of supply to the third container are set within the low-temperature region or the low-pressure region, the temperature (T3) in the third container is set to a specific condition, specifically each of the conditions (C1) and (C2), under the pressure condition of p1>P2, whereby the component held in the first container can be stably supplied.

In step (C), the temperature (T2) and pressure (P2) in the second container 2 are not limited. The temperature and pressure of the component held in the second container within the second container 2 are the same as the temperature (T2) and pressure (P2); however, the temperature (t2) and pressure (p2) of the component held in the second container at the time of supply to the third container 3 can be adjusted, for example, by the following means.

In general, when the component held in the second container is supplied to the third container, a supply pipe is provided to connect the second container and the third container, and the component held in the second container is supplied through the supply pipe to the third container. The supply pipe that connects the second container and the third container generally has means for turning on and off the supply of the second component and controlling the amount of supply per hour, and also has, if necessary, a pressure adjusting means and a temperature adjusting means.

In step (C), in order to achieve p2>P3, which is an essential condition for this step, a pressure adjusting means, typically a pump, provided in the supply pipe is generally used.

In step (C), in order to maintain the temperature (T3) and pressure (P3) in the third container within the low-temperature region or the low-pressure region from the start of supply of the component held in the first container and the component held in the second container to the third container to the end of mixing in the third container, it is preferable to set the temperature (t1) and pressure (p1) of the component held in the first container at the time of supply to condition (C1) or (C2), and to adjust the temperature (t2) and pressure (p2) of the component held in the second container at the time of supply to the third container, and further the amount of supply per hour, so that the temperature (T3) and pressure (P3) are within the above range. It is preferable to also adjust the amount of supply per hour of the component held in the first container.

For example, when the temperature (T3) and pressure (P3) in the third container are in the low-temperature region, the temperature (t2) and pressure (p2) of the component held in the second container at the time of supply are set within the low-temperature region. Further, when the temperature (T3) and pressure (P3) in the third container are in the low-pressure region, for example, the temperature (t2) and pressure (p2) of the second component at the time of supply are set within the low-pressure region. In this case, in more stable conditions, for example, the pressure (p2) is within the low-pressure region and $t2<(1.22-P3)/0.0032$.

As is the case above, when the component held in the first container and the component held in the second container are mixed, it is preferable to mix both components in a liquid state, in terms of efficiency.

In order to apply this condition, for example, the first component is held as a liquid at less than 15° C. in the first container. In general, it is preferable to store the component held in the first container in a state in which gas and liquid coexist. Therefore, the temperature (T1) and pressure (P1) in the first container are preferably adjusted at a temperature of less than 15° C. and on the vapor pressure curve of difluoroethylene. Similarly, the component held in the second container is held as a liquid at less than 15° C. in the second container.

The component held in the first container and the component held in the second container both as liquids at less than 15° C. prepared in the above manner are supplied in such a manner that the component held in the first container is supplied in a liquid state at less than 15° C. so as to comply with condition (C1), and the component held in the second container is supplied in a liquid state at less than 15° C., while ensuring the relationship of p2>P3, to the third container that is maintained in the low-temperature region. In step (C), the component held in the first container and the component held in the second container can be preferably mixed both in a liquid state in the third container, as described above.

FIG. 6

FIG. 6 schematically shows an example of step (C) of supplying both the component held in the first container and the component held in the second container to the third container when the component held in the first container and the component held in the second container are both liquids at less than 15° C.

FIG. 6 (7a) shows a state of the component 11 held in the first container and the component 12 held in the second container before being supplied to the third container 3, and FIG. 6 (7b) shows a state in which the component 11 held in the first container and the component 12 held in the second container are supplied to the third container 3 to obtain a working medium 13.

The first container 1 that holds the component 11 held in the first container and the second container 2 that holds the component 12 held in the second container shown in FIG. 6 (7a) can be prepared in the same manner as in step (A).

FIG. 6 shows the operation to supply both the component (liquid) 11 held in the first container 1 and the component (liquid) 12 held in the second container 2 to the third container 3.

In FIG. 6, the first container 1 and the second container 2 each have one discharge port, and the third container 3 has two supply ports. The discharge ports of the first container 1 and second container 2 are each connected to the two supply ports of the third container 3 through pumps 15 and 16 by supply pipes 7 and 8 and supply pipes 9 and 10, through which gas or liquid can flow. The component 11 held in the first container within the first container 1 and the component 12 held in the second container within the second container 2 respectively move from the discharge port of the first container 1 and the discharge port of the second container 2 to the supply ports of the third container 3 through the pumps 15 and 16 within the supply pipes 7 and 8, and the supply pipes 9 and 10, and are supplied into the third container 3.

In FIG. 6, the component 11 held in the first container and the component 12 held in the second container are both supplied into the third container 3, whereby the component 11 held in the first container and the component 12 held in the second container are mixed in the third container 3 to obtain a working medium 13. The supply of the component 11 held in the first container and the supply of the component 12 held in the second container are generally performed at the same time. In that case, the amount of the component 11 held in the first container and the amount of the component 12 held in the second container supplied to the third container 3 are preferably adjusted so that the formulation of a reservoir stored, as needed, in the third container becomes the formulation of the target working medium along with the supply of these components. Alternatively, a means capable of continuously measuring the formulation of the reservoir in the third container 3 may be provided, and the component 11 held in the first container and the component 12 held in the second container may be both supplied while adjusting their supply amounts, as needed, until a necessary amount of the working medium of the target formulation is produced.

In this example, the conditions for performing step (C) correspond to (C1) above. Therefore, the temperature (T3) in the third container 3 is maintained at less than 15° C. at least from the start of supply of the component held in the first container to the end of mixing of the component held in the first container and the component held in the second container.

In FIG. 6, if necessary, after a specific amount of the component 11 held in the first container is first supplied to the third container 3, a specific amount of the component 12 held in the second container may be supplied to the third container 3. Alternatively, after a specific amount of the component 12 held in the second container is first supplied to the third container 3, a specific amount of the component 11 held in the first container may be supplied to the third container 3.

In the former of these cases, the target working medium can be stably produced by handling the component held in the first container and the component held in the second container under the same conditions as in step (B). In the latter case, the target working medium can be stably produced by handling the component held in the first container and the component held in the second container under the same conditions as in step (A).

According to the production method of the present invention, when the component held in the second container is supplied to the third container in step (C), components held in a plurality of the same or different second containers may be supplied from each of the second containers. In this case, the supply of the component held in the first container and the supply of the components held in the plurality of second containers to the third container may be performed at the same time according to the conditions of the production method of the present disclosure, or either of the components may be supplied in advance.

In the production method of the present invention, the component held in the specific container is supplied into the first, second, or third container, whereby the component held in the first container and the component held in the second container are mixed in this container while continuously varying their formulations, and finally a working medium is obtained.

At the time of the supply, for the purpose of suppressing a state in which the component held in the first container and the component held in the second container are present non-uniformly depending on the position thereof in the container to which the component held in the specific container is supplied, it is preferable to supply the component held in the specific container using a pump. While suitably adjusting the pump discharge pressure, the component held in the specific container is supplied into the container, and the component held in the first container and the component held in the second container are uniformly mixed in the container, whereby it is possible to prevent, in the container, non-uniformity of the component concentration held in the container.

When the component held in the specific container is supplied into the first, second, or third container, it is preferable to insert the end of the supply pipe into the liquid phase of the component present in the first, second, or third container, because the concentration of each component can be prevented from becoming non-uniform depending on the position thereof in the container.

In the container in which the component held in the first container and the component held in the second container are mixed, in order to prevent the concentration of each component from becoming non-uniform depending on the position thereof, a means for preventing non-uniformity of the component concentration, such as stirring, may be used in each container.

The working medium obtained by the production method of the present disclosure is confirmed not to have self-decomposition properties under temperature and pressure conditions for use as a working medium.

When the working medium produced in the first, second, or third container is placed in a subdividing container or the like, it is not necessary to strictly control the temperature and pressure conditions. For example, when the working medium is transferred from the container in which it is produced to a subdividing container, it is stable when transferred at a pressure and temperature in the region above the self-decomposition border line of difluoroethylene.

However, the conditions for subdividing are preferably such that the working medium produced in the first, second, or third container is maintained at −40° C. to 15° C., preferably −20° C. to 0° C., and transferred to a subdividing container through a pump at a pump discharge pressure, as gauge pressure, of 0.1 MPaG to 3.0 MPaG, preferably 0.3 MPaG to 2.0 MPaG.

Embodiments of the method for producing a working medium of the present invention are described above with reference to examples; however, the production method of the present invention is not limited to the above embodiments. The configuration thereof can be suitably changed, if necessary, without departing from the gist of the present invention.

Item 1. A method for producing a working medium containing difluoroethylene, comprising mixing a first component containing difluoroethylene at a ratio of more than 65 mol % and held in a first container, and a second component without self-decomposition properties held in a second container, by the following step (A), (B), or (C), the working medium containing difluoroethylene at a ratio of 65 mol % or less based on the entire amount.

Step (A)

The component held in the first container is supplied to the second container under the following condition (A1) or (A2).

Condition (A1)

The temperature (t1) of the component held in the first container at the time of the supply is t1<15° C., the relationship between the gauge pressure (P2) in the second container and the gauge pressure (p1) of the component held in the first container at the time of the supply is p1>P2 at least from the start of the supply to the end of the mixing, and the temperature (T2) in the second container is maintained in a state of T2<15° C.

Condition (A2)

The component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P2) in the second container and the gauge pressure (p1) of the component held in the first container is p1>P2 at least from the start of the supply to the end of the mixing, and the temperature (T2) in the second container is maintained in a state of T2≤180° C. and T2<(1.22−p1)/0.0032.

Step (B)

The component held in the second container is supplied to the first container under the following conditions (B1) and (B2).

Condition (B1)

The temperature (T1) and gauge pressure (P1) in the first container are maintained in a state of T1<15° C. or in a state of 15° C.≤T1≤180° C. and P1 [MPaG]<1.22−0.0032T1 at least from the start of the supply to the end of the mixing.

Condition (B2)

The gauge pressure (p2) of the component held in the second container is p2>P1 at least at the time of the supply.

Step (C)

The component held in the first container is supplied to a separately prepared third container under the following condition (C1) or (C2), while maintaining the temperature (T3) and gauge pressure (P3) in the third container in a state of T3<15° C. or in a state of 15° C.≤T3≤180° C. and P3 [MPaG]<1.22−0.0032T3 at least from the start of the following supply to the end of the mixing, and the component held in the second container is supplied so that the gauge pressure (p2) thereof is p2>P3 at least at the time of supply thereof.

Condition (C1)

The temperature (t1) of the component held in the first container at the time of the supply is t1<15° C., the relationship between the gauge pressure (P3) in the third container and the gauge pressure (p1) of the component held in the first container at the time of the supply is p1>P3 at least from the start of the supply to the end of the mixing, and the temperature (T3) in the third container is maintained in a state of T3<15° C.

Condition (C2)

The component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P3) in the third container and the gauge pressure (p1) of the component held in the first container is p1>P3 at least from the start of the supply to the end of the mixing, and the temperature (T3) in the third container is maintained in a state of T3≤180° C. and T3<(1.22−p1)/0.0032.

Item 2. The method for producing a working medium according to Item 1, wherein the difluoroethylene is at least one member selected from the group consisting of 1,1-difluoroethylene (HFO-1132a), cis-1,2-difluoroethylene (HFO-1132(Z)), and trans-1,2-difluoroethylene (HFO-1132(E)).

Item 3. The method for producing a working medium according to Item 1 or 2, wherein the component held in the second container is at least one member selected from the group consisting of saturated hydrofluorocarbons, unsaturated hydrofluorocarbons, unsaturated hydrochlorofluorocarbons, and unsaturated chlorofluorocarbons.

Item 4. The method for producing a working medium according to Item 3, wherein the component held in the second container contains a component without self-decomposition properties at a ratio of 35 mol % or more.

Item 5. The method for producing a working medium according to any one of Items 1 to 4, wherein the component held in the second container contains 2,3,3,3-tetrafluoropropene and/or difluoromethane.

Item 6. The method for producing a working medium according to any one of Items 1 to 5, wherein the working medium obtained by mixing the component held in the first container and the component held in the second container is a working medium containing difluoroethylene and 2,3,3,3-tetrafluoropropene, the ratio of the total amount of difluoroethylene and 2,3,3,3-tetrafluoropropene based on the entire amount of the working medium is 65 mol % to 100 mol %, and the ratio of difluoroethylene based on the total amount of difluoroethylene and 2,3,3,3-tetrafluoropropene is 1 mol % to 65 mol %.

Item 7. The method for producing a working medium according to any one of Items 1 to 5, wherein the working medium obtained by mixing the component held in the first container and the component held in the second container is a working medium containing difluoroethylene and difluoromethane, the ratio of the total amount of difluoroethylene and difluoromethane based on the entire amount of the working medium is 65 mol % to 100 mol %, and the ratio of difluoroethylene based on the total amount of difluoroethylene and difluoromethane is 1 mol % to 65 mol %.

Item 8. The method for producing a working medium according to any one of Items 1 to 5, wherein the working medium obtained by mixing the component held in the first container and the component held in the second container is a working medium containing difluoroethylene, 2,3,3,3-tetrafluoropropene, and difluoromethane, the ratio of the total amount of difluoroethylene, 2,3,3,3-tetrafluoropropene, and difluoromethane based on the entire amount of the working medium is 65 mol % to 100 mol %, and based on the total amount of difluoroethylene, 2,3,3,3-tetrafluoropropene, and difluoromethane, the ratio of difluoroethylene is 1 mol % to 65 mol %, the ratio of 2,3,3,3-tetrafluoropropene is 98 mol % or less, and the ratio of difluoromethane is 98 mol % or less.

Item 9. The method for producing a working medium according to any one of Items 1 to 8, wherein the component held in the first container comprises difluoroethylene.

Item 10. The method for producing a working medium according to Item 8, wherein the component held in the second container comprises a mixture of 2,3,3,3-tetrafluoropropene and difluoromethane.

Item 11. The method for producing a working medium according to any one of Items 1 to 4, wherein the component held in the second container comprises trans-1,3,3,3-tetrafluoropropene.

Item 12. The method for producing a working medium according to any one of Items 1 to 4, wherein the component held in the second container comprises a mixture of trans-1,3,3,3-tetrafluoropropene and difluoromethane.

Item 13. The method for producing a working medium according to any one of Items 1 to 4, wherein in step (A), the temperature in the first container and the temperature in the second container are both maintained at less than 15° C., and the component held in the first container is supplied in a liquid state at t1<15° C. to the second container.

Item 14. The method for producing a working medium according to any one of Items 1 to 4, wherein in step (B), the temperature in the first container and the temperature in the second container are both maintained at less than 15° C., and the component held in the second container is supplied in a liquid state at t2<15° C. to the first container.

Item 15. The method for producing a working medium according to any one of Items 1 to 4, wherein in step (C), the temperature in the first container, the temperature in the second container, and the temperature in the third container are all maintained at less than 15° C., and the component held in the first container is supplied in a liquid state at t1<15° C. and the component held in the second container is supplied in a liquid state at t2<15° C. to the third container.

EXAMPLES

The present disclosure is described below with reference to Examples; however, the present disclosure is not limited to these Examples and the like.

(1) Filling Example 1

Example of Supplying Trans-1,2-Difluoroethylene (HFO-1132(E)) (Liquid) to Container Holding Second Component Liquid This is an example of forming 30 kg of a mixed refrigerant of HFO-1132(E)/HFC-32=65/35 mol % in a second container.

A first container is filled with 18 kg of HFO-1132(E) cooled to 10° C. The pressure in the first container at this time is 1.0 MPaG. The second container is filled with 12 kg of HFC-32 cooled to −30° C. The pressure in the second container at this time is 0.17 MPaG. 18 kg of HFO-1132(E) cooled to 0° C. is transferred from the first container to the second container. At this time, the temperature of the supply pipe is 10° C., and the pressure is 1.0 MPaG. During the filling operation, HFO-1132(E) in the first container and the composition in the second container are always in a state in which they are not self-decomposed.

The composition of HFO-1132(E)/HFC-32=65/35 mol % formed by this operation in the second container is a composition that has been confirmed to have no self-decomposition properties under temperature and pressure conditions for use as a working medium. Further, the composition formed in the second container is liquid-compressed to 1.5 MPaG at 10° C. using a liquid feed pump, and placed in subdividing containers for shipping products.

(2) Filling Example 2

Example of Supplying Second Component (Liquid) to Container Holding Trans-1,2-Difluoroethylene (HFO-1132(E)) Liquid This is an example of forming 30 kg of a mixed refrigerant of HFO-1132(E)/HFC-32=65/35 mol % in a first container.

The first container is filled with 18 kg of HFO-1132(E) cooled to −30° C. The pressure in the first container at this time is 0.18 MPaG. A second container is filled with 12 kg of HFC-32 cooled to 10° C. The pressure in the second container at this time is 1.0 MPaG. 12 kg of HFC-32 cooled to 10° C. is transferred from the second container to the first container. At this time, the temperature of the supply pipe is 10° C., and the pressure is 1.0 MPaG. During the filling operation, the composition in the first container is always in a state in which it is not self-decomposed.

(3) Filling Example 3

Example of Supplying Trans-1,2-Difluoroethylene (HFO-1132(E)) Difluoroethylene (Liquid) and Second Component (Liquid) to Third Container This is an example of forming 30 kg of a mixed refrigerant of HFO-1132(E)/HFC-32=65/35 mol % in a third container.

A second container is filled with 12 kg of HFC-32 cooled to −30° C. The pressure in the second container at this time is 0.17 MPaG. A separate first container is filled with 18 kg of HFO-1132(E) cooled to 10° C. The pressure in the first container at this time is 1.0 MPaG. 12 kg of HFC-32 cooled to −30° C. is transferred from the second container to the third container under conditions in which the temperature of the supply pipe is −30° C. and the pressure is 0.17 MPaG. Then, 18 kg of HFO-1132(E) cooled to 10° C. is transferred from the first container to the third container under conditions in which the temperature of the supply pipe is 10° C. and the pressure is 1.0 MPaG. During the filling operation, HFO-1132(E) in the first container and the composition in the third container are always in a state in which they are not self-decomposed.

INDUSTRIAL APPLICABILITY

Working media obtained by the method for producing a working medium of the present disclosure can be handled with high stability, and are useful as refrigerants for freezing and refrigerating equipment (e.g., built-in showcases, separate showcases, commercial freezers and refrigerators, vending machines, and ice makers), refrigerants for air-conditioning systems (e.g., room air conditioners, packaged air conditioners for shops, packaged air conditioners for buildings, packaged air conditioners for facilities, gas engine heat pumps, air conditioners for trains, and air conditioners for vehicles), working fluids for power generation systems (e.g., waste heat recovery power generation), working media for heat transport equipment (e.g., heat pipes), or media for secondary cooling machines.

REFERENCE SIGNS LIST

1. First container
2. Second container
3. Third container
7, 8, 9, 10. Supply pipe
11. First component
12. Second component
13. Working medium
14, 15, 16. Pump

The invention claimed is:

1. A method for producing a working medium containing difluoroethylene, comprising mixing a first component containing difluoroethylene at a ratio of more than 65 mol % and held in a first container, and a second component without self-decomposition properties held in a second container, by the following step (A), (B), or (C), the working medium containing difluoroethylene at a ratio of 65 mol % or less based on the entire amount,
   wherein, in step (A),
      the component held in the first container is supplied to the second container under the following condition (A1) or (A2),
      wherein, in condition (A1),
      the temperature (t1) of the component held in the first container at the time of the supply is t1<15° C., the relationship between the gauge pressure (P2) in the second container and the gauge pressure (p1) of the component held in the first container at the time of the supply is p1>P2 at least from the start of the supply to the end of the mixing, and the temperature (T2) in the second container is maintained in a state of T2<15° C., and
      wherein, in condition (A2),
      the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P2) in the second container and the gauge pressure (p1) of the component held in the first container is p1>P2 at least from the start of the supply to the end of the mixing, and the temperature (T2) in the second container is maintained in a state of T2≤180° C. and T2<(1.22−p1)/0.0032,
   wherein, in step (B),
      the component held in the second container is supplied to the first container under the following conditions (B1) and (B2),
      wherein, in condition (B1),
      the temperature (T1) and gauge pressure (P1) in the first container are maintained in a state of T1<15° C. or in a state of 15° C.≤T1≤180° C. and P1 [MPaG] <1.22−0.0032T1 at least from the start of the supply to the end of the mixing, and
      wherein, in condition (B2),
      the gauge pressure (p2) of the component held in the second container is p2>P1 at least at the time of the supply, and
   wherein, in step (C),
      the component held in the first container is supplied to a separately prepared third container under the following condition (C1) or (C2), while maintaining the temperature (T3) and gauge pressure (P3) in the third container in a state of T3<15° C. or in a state of 15° C.≤T3≤180° C. and P3 [MPaG]<1.22−0.0032T3 at least from the start of the following supply to the end of the mixing, and the component held in the second container is supplied so that the gauge pressure (p2) thereof is p2>P3 at least at the time of supply thereof,
      wherein, in condition (C1),
      the temperature (t1) of the component held in the first container at the time of the supply is t1<15° C., the relationship between the gauge pressure (P3) in the third container and the gauge pressure (p1) of the component held in the first container at the time of the supply is p1>P3 at least from the start of the supply to the end of the mixing, and the temperature (T3) in the third container is maintained in a state of T3<15° C., and
      wherein, in condition (C2),
      the component held in the first container at the time of the supply is in a gaseous state in which the temperature (t1) thereof is 15° C.≤t1≤180° C. and the gauge pressure (p1) thereof is p1 [MPaG]<1.22−0.0032t1, the relationship between the gauge pressure (P3) in the third container and the gauge pressure (p1) of the component held in the first container is p1>P3 at least from the start of the supply to the end of the mixing, and the temperature (T3) in the third container is maintained in a state of T3≤180° C. and T3<(1.22−p1)/0.0032.

2. The method for producing a working medium according to claim 1, wherein the difluoroethylene is at least one member selected from the group consisting of 1,1-difluoroethylene (HFO-1132a), cis-1,2-difluoroethylene (HFO-1132(Z)), and trans-1,2-difluoroethylene (HFO-1132(E)).

3. The method for producing a working medium according to claim 1, wherein the component held in the second container is at least one member selected from the group consisting of saturated hydrofluorocarbons, unsaturated hydrofluorocarbons, unsaturated hydrochlorofluorocarbons, and unsaturated chlorofluorocarbons.

4. The method for producing a working medium according to claim 3, wherein the component held in the second container contains a component without self-decomposition properties at a ratio of 35 mol % or more.

5. The method for producing a working medium according to claim 1, wherein the component held in the second container contains 2,3,3,3-tetrafluoropropene and/or difluoromethane.

6. The method for producing a working medium according to claim 1, wherein the working medium obtained by mixing the component held in the first container and the component held in the second container is a working medium containing difluoroethylene and 2,3,3,3-tetrafluoropropene, the ratio of the total amount of difluoroethylene and 2,3,3,3-tetrafluoropropene based on the entire amount of the working medium is 65 mol % to 100 mol %, and the ratio of difluoroethylene based on the total amount of difluoroethylene and 2,3,3,3-tetrafluoropropene is 1 mol % to 65 mol %.

7. The method for producing a working medium according to claim 1, wherein the working medium obtained by mixing the component held in the first container and the component held in the second container is a working medium containing difluoroethylene and difluoromethane, the ratio of the total amount of difluoroethylene and difluoromethane based on the entire amount of the working medium is 65 mol % to 100 mol %, and the ratio of difluoroethylene based on the total amount of difluoroethylene and difluoromethane is 1 mol % to 65 mol %.

8. The method for producing a working medium according to claim 1, wherein the working medium obtained by mixing the component held in the first container and the component held in the second container is a working medium containing difluoroethylene, 2,3,3,3-tetrafluoropropene, and difluoromethane, the ratio of the total amount of difluoroethylene, 2,3,3,3-tetrafluoropropene, and difluoromethane based on the entire amount of the working medium is 65 mol % to 100 mol %, and based on the total amount of difluoroethylene, 2,3,3,3-tetrafluoropropene, and difluoromethane, the ratio of difluoroethylene is 1 mol % to 65 mol %, the ratio of 2,3,3,3-tetrafluoropropene is 98 mol % or less, and the ratio of difluoromethane is 98 mol % or less.

9. The method for producing a working medium according to claim 1, wherein the component held in the first container comprises difluoroethylene.

10. The method for producing a working medium according to claim 8, wherein the component held in the second container comprises a mixture of 2,3,3,3-tetrafluoropropene and difluoromethane.

11. The method for producing a working medium according to claim 1, wherein the component held in the second container comprises trans-1,3,3,3-tetrafluoropropene.

12. The method for producing a working medium according to claim 1, wherein the component held in the second container comprises a mixture of trans-1,3,3,3-tetrafluoropropene and difluoromethane.

13. The method for producing a working medium according to claim 1, wherein in step (A), the temperature in the first container and the temperature in the second container are both maintained at less than 15° C., and the component held in the first container is supplied in a liquid state at t1<15° C. to the second container.

14. The method for producing a working medium according to claim 1, wherein in step (B), the temperature in the first container and the temperature in the second container are both maintained at less than 15° C., and the component held in the second container is supplied in a liquid state at t2<15° C. to the first container.

15. The method for producing a working medium according to claim 1, wherein in step (C), the temperature in the first container, the temperature in the second container, and the temperature in the third container are all maintained at less than 15° C., and the component held in the first container is supplied in a liquid state at t1<15° C. and the component held in the second container is supplied in a liquid state at t2<15° C. to the third container.

* * * * *